United States Patent [19]

Crampton

[11] 4,270,743
[45] Jun. 2, 1981

[54] FORWARD NUMBERING OR UNDERLAP SHEET DELIVERY

[75] Inventor: Charles P. Crampton, Hamilton, Ohio

[73] Assignee: Hamilton Tool Company, Hamilton, Ohio

[21] Appl. No.: 920,364

[22] Filed: Jun. 29, 1978

[51] Int. Cl.³ .......................................... B65H 39/06
[52] U.S. Cl. .................................... 270/58; 271/182
[58] Field of Search ................. 270/58, 59; 271/202, 271/270, 182, 183, 229; 198/423, 462; 83/88

[56] References Cited

U.S. PATENT DOCUMENTS

| 1,632,433 | 6/1927 | Christman | 270/58 |
| 3,026,107 | 3/1962 | Stroud | 270/58 |
| 3,228,273 | 1/1966 | Huffman | 83/88 |
| 3,373,666 | 3/1966 | Crampton | 93/93 |
| 3,599,805 | 8/1971 | Spencer | 214/6 H |
| 3,861,515 | 1/1975 | Runyan | 271/202 |
| 4,136,865 | 1/1979 | Marass | 271/270 |

Primary Examiner—Edward M. Coven
Assistant Examiner—Heinz A.
Attorney, Agent, or Firm—Kinney & Schenk

[57] ABSTRACT

A plurality of consecutively numbered sheets or parcels of paper sheets such as, by way of example, snapout forms or the like are consecutively deposited onto the upper reach of a conveyor whereby the leading edge of each subsequent form is inserted beneath the trailing portion of the preceding form whereby an underlap-echelon relationship of the succeeding individual forms is provided, and wherein the forms are numbered consecutively and forwardly with the lowest numbered sheet foremost and on top of the sheets or forms on the conveyor.

14 Claims, 1 Drawing Figure

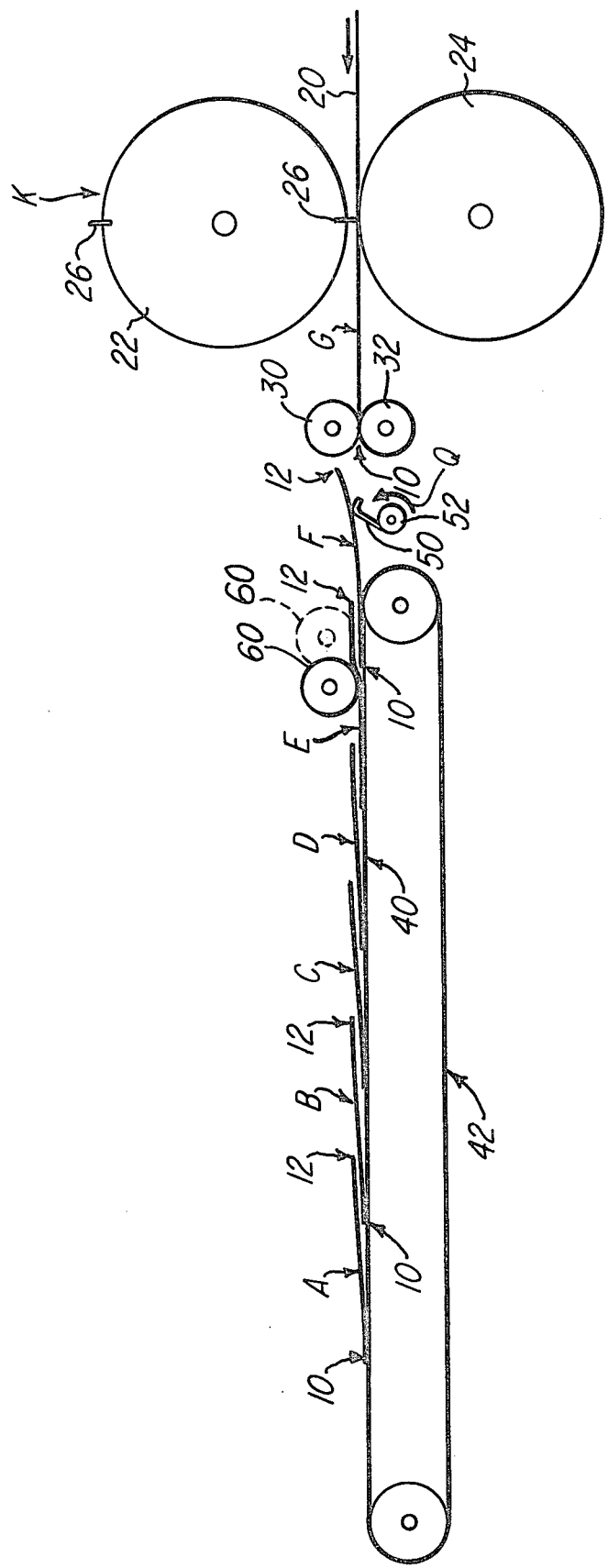

FORWARD NUMBERING OR UNDERLAP SHEET DELIVERY

BACKGROUND OF THE INVENTION

1. Field of the Invention

The present invention is directed to simple, yet highly effective means for, and a method of effecting forward numbering, that is the underlap delivery of a plurality of consecutively numbered individual sheets or a plurality of consecutively numbered parcels of sheets which are deposited on a conveyor and advanced thereby in an underlap echelon relationship wherein each succeeding sheet or parcel of sheets having a higher number is located beneath each preceding sheet or parcel of sheets having the next lower number.

2. Description of Prior Art

Applicant's U.S. Pat. No. 3,373,666 is directed to a batch delivery mechanism, wherein a plurality of individual sheets or individual parcels of sheets are sequentially deposited onto an endless conveyor as best illustrated in FIGS. 1, 2, 5 and 6 wherein each succeeding or consecutively higher numbered sheet is deposited in overlying relationship with each preceding or consecutively lower numbered sheet whereby the numbers of the sheets thus delivered and stacked are characterized by backward or reverse numbering in that the sequence of numbers runs from a lower number on the bottom to a higher number on the top of the stack.

U.S. Pat. No. 3,599,805 of H. J. Spencer entitled Unit-Handling Apparatus, discloses expensive and complicated means for flipping over or inverting each "unit set" as it issues from a collator. Spencer, in Col. 2, lines 17-31 states:

"This is achieved through a gripping mechanism which is particularly advantageous for producing consecutively numbered sets. A unit set is given a number on its topmost sheet and a given run may include 10,000 unit sets. By flipping each unit set over as it issues from the machine, each stack will have at its bottom the lowest numbered unit set. Hence, the unit sets in stack 38 will be numbered on their bottom-facing side from 1 to 50 in proceeding from the bottom to the top and the stack 38a similarly arranged but numbered, for example, from 51 to 100. Thus, by inverting the stack 38, the lowest numbered unit set is positioned uppermost and aggregated stacks can be provided wherein the unit sets are consecutively numbered. Were it not for the inverting step provided at 39, it would be necessary to number the unit sets in reverse fashion which presents substantial operating difficulties."

The mechanism required to handle Spencer's "unit sets" is illustrated in FIGS. 2-12 of his patent.

SUMMARY OF THE INVENTION

The delivery mechanism of the subject invention has been designed whereby the tail end of each preceding sheet or the tail end of each preceding parcel of sheets is momentarily lifted for permitting the forward or leading edge of the next sheet or the leading edge of the next succeeding parcel of sheets to be slid or advanced forwardly under the rear or tail end portion of the preceding sheet or parcel of sheets whereby an underlap echelon relationship of the delivered sheets or parcel of sheets is provided. The aforesaid arrangement makes it convenient and commercially feasible to provide forward numbering to the individual sheets or individual parcels of sheets whereby the sheets as delivered to the conveyor are consecutively numbered with the lower numbers uppermost thereby avoiding the necessity of rehandling the sheets for placing them in a downwardly increasing numerical sequence.

BRIEF DESCRIPTION OF THE DRAWING

The FIGURE is a diagrammatic side view of a typical mechanism which embodies the teachings of the present invention.

DESCRIPTION OF THE PREFERRED EMBODIMENT

At the outset it should be understood that the term sheet as used herein refers not only to a single sheet or to a parcel or plurality of collated sheets, such as by way of example, are used in snapout forms but wherein each sheet whether of single or multiple ply will have a front or leading edge 10, a rear or trailing edge 12, and side edges.

The numeral 20 denotes generally an endless web of material which may be of single or multiple ply, said web being suitably fed by means, not illustrated, to a cut-off station K which includes a cut-off blade 22 and a hard anvil cylinder 24. The knives indicated generally by a numeral 26 sever the web into similar size consecutive sheets or similar size parcels of sheets each having a leading edge 10 and a trailing edge 12.

The leading edge 10 of the last severed sheet G is introduced between driven rollers 30 and 32 which rotate at peripheral speeds greater than the speed at which web 20 is introduced to the cut-off station for thereby separating the trailing end of sheet G from the leading edge of the next sheet or parcels of sheets to be severed from web 20. Driven rollers 30 and 32 impart a positive pulling action to sheet G which is thereby moved or advanced at an accelerated rate in a forward direction (to the left in the drawing) whereby its forward end 10 is introduced beneath the elevated trailing edge 12 of the preceding sheet F whose leading edge 10 was previously inserted and slid under trailing edge 12 of preceding sheet E, said latter sheet being supported on the upper reach 40 of an endless conveyor 42.

Means in the form of a lifter arm 50 secured to and carried by a rotatable shaft 52 is mounted as illustrated whereby to be rotated in timed relationship with respect to the accelerated sheet-advancing speed of rollers 30 and 32 whereby the trailing end 12 of each preceding sheet will be lifted upwardly, as illustrated, whereby the leading edge 10 of the next succeeding sheet may be advanced forwardly of and slid under the rear portion of the preceding sheet whose forward portion has been deposited on the upstream (right) end of the upper reach 40 of the conveyor 42.

The slow-down wheel 60 likewise provides what can be referred to as a transverse abutment intermediate the overall length of the last sheet (E) under whose rear portion the forward portion of the next succeeding sheet (f) has been advanced. Said abutment is engaged by the leading edge 10 the the said next succeeding sheet which, as earlier noted, is advanced at a rate of travel which is greater than the rate of travel of web 20.

In the amount or degree of initial "underlap" may be conveniently changed and/or sheets of different lengths accommodated by moving the slow-down wheel further toward or from the upstream end of the conveyor.

Uniformly satisfactory results have been obtained in those instances in which conveyor speed 42 is from 3% to 75% of web speed 20.

Slow-down wheel 60, which in the preferred embodiment of the invention is provided with a variable speed drive, effectively limits and determines the amount of overlap of the rear portion of each preceding sheet with respect to the forward portion of the underlying succeeding sheet. In the illustration, the forward portion of each succeeding sheet extends about half way under the next preceding sheet.

In those instances in which the continuous web 20 has been preprinted with a repetitious sheet pattern and wherein the sheet or parcel of sheets of each pattern have been consecutively numbered, the numbering of the individual sheets, whether of single or multiple ply, will consecutively increase from a lower number to the next higher number with the lower numbered sheet in every instance foremost, that is on top of the next higher numbered sheet. In the drawing it will be noted that sheet A will be on top of sheet B, and sheet B will be on top of sheet C, etc. as the individual sheets are deposited on and then advanced on the upper reach 40 of the conveyor, and said sheet-relationship will, of course, be maintained when the sheets are submitted to a conventional stacking or jogging operation at or adjacent the discharge end of the conveyor.

The subject device has the inherent advantage of eliminating the curl problem at the leading edge of each last severed sheet, which problem has made it necessary in the case of conventional batch delivery or backward numbering devices to provide endless hold-down bands and/or brush wheels immediately above the upper reach of a conveyor for counteracting and flattening the curl at the forward edge of the severed sheets.

The advancement of the leading edge 10 of each successively cut sheet beneath the trailing edge of each preceding sheet effectively eliminates the problem of curl since the positioning of each leading edge under, rather than over, each preceding sheet effectively flattens out and eliminates any tendency for the curl to present a problem.

The high speed gripper rolls 30 and 32 are, as earlier indicated, not only driven at peripheral speeds in excess of the web speed, but said gripper rolls are also suitably mounted for movement toward or from a vertical center line extending through the rollers 22 and 24 of the cut-off station. Said movement is desirable in order to accommodate sheets or parcels of sheets of varying lengths.

By the same token, the rotatably driven slowdown wheel 60 is also suitably mounted for movement relative to the gripper roller assembly since the location of the slow-down wheel 60 determines the amount by which the rear portion of each preceding or upper sheet overlaps the forward portion of the next succeeding sheet.

The outer end of the lifter finger 50 is somewhat rounded as illustrated whereby rotation of said finger in the direction as indicated by the headed arrow Q will engage the undersurface of each preceding sheet immediately in advance of the trailing edge thereof whereby said trailing end 12 will be fully elevated or lifted by the time leading edge 10 of the next succeeding sheet is advanced at a speed greater than the web speed under said elevated trailing end.

It should be understood that suitable conventional driving means, not illustrated, are utilized to provide and correlate the speed of rotation of lifter 50 relative to the speed of advancement of each last severed sheet, such as G, in the drawing. Since such variable speed driving mechanisms are old in the art they have not been illustrated, particularly since the inventive concept is neither directed to, concerned with or limited by any particular drive means.

What is claimed is:

1. A device for delivering in underlap echelon relationship a plurality of similar size, flat, sheet-like articles onto the upper reach of an endless conveyor wherein the forward portion of each succeeding article is located beneath the rear portion of each preceding article, comprising:

means for continuously and sequentially providing a plurality of individual, similar size, flat, sheet-like articles of uniform length adjacent the upstream end of an endless conveyor;

means in advance of the upstream end of said conveyor for accelerating the rate of travel of each individual article toward the upstream end of said conveyor and depositing it on an upper reach thereof;

means between said last mentioned means and the upstream end of said conveyor for elevating the trailing edge of that individual article whose leading edge and forward portion has been last deposited onto the upper reach of said conveyor such that the leading edge of the next succeeding article is deposited on the upstream end of the upper reach of said conveyor beneath the elevated trailing edge of the preceding article; and a rotatably driven slow down roll at the upstream end of the conveyor for limiting the amount by which the leading edge of each succeeding article is advanced under and relative to the undersurface of the preceding article last deposited on the conveyor, the periphery of the slow down roll being operative to exert pressure against the upper surface of the last article deposited on the conveyor, intermediate the length of said article to provide an abutment transversely of said article which is engaged by the leading edge of the next succeeding article as it is advanced beneath and forwardly of the trailing edge of the preceding article, the slow down roll being movable toward and away from the upstream end of the conveyor for varying the degree to which the leading edge of the next succeeding article is deposited on the upstream end of the upper reach of said conveyor beneath the elevated trailing edge of the preceding article.

2. A device for delivering in underlap echelon relationship a plurality of similar size, flat, sheet-like articles onto the upper reach of an endless conveyor wherein the forward portion of each succeeding article is located beneath the rear portion of each preceding article, comprising:

means for continuously and sequentially providing a plurality of individual, similar size, flat, sheet-like articles of uniform length adjacent the upstream end of an endless conveyor;

means in advance of the upstream end of said conveyor for accelerating the rate of travel of each individual article toward the upstream end of said conveyor and depositing it on an upper reach thereof;

a rotatable shaft having a lifter finger projecting therefrom to engage the undersurface of an article last deposited on the conveyor at a location adjacent to but in advance of the trailing edge of said article, said rotatable shaft being rotated about an axis positioned below the conveyor elevation in timed relationship with the rate of travel of said articles so that the lifter finger engages the underside edge and rear portion of said last deposited article in timed sequence with the advance of the leading edge of the next advanced article; and slow down means at the upstream end of the conveyor for limiting the amount of which the leading edge of each succeeding article is advanced under and relative to the undersurface of the preceeding article last deposited on the conveyor, the slow down means being operative to exert pressure against the last article deposited on the conveyor, intermediate the length of said article to provide an abutment transversely of said article which is engaged by the leading edge of the next succeeding article as it is advanced beneath and forwardly of the trailing edge of the preceding article, the slow down means being movable toward and away from the upstream end of the conveyor for varying the degree to which the leading edge of the next succeeding article is deposited on the upstream end of the upper reach of said conveyor beneath the elevated trailing edge of the preceding article.

3. A device as called for in claim 2, wherein the means for continuously and sequentially providing a plurality of individual articles, as aforesaid, includes a cut-off station where an endless web of sequentially connected, repetitious articles is severed into individual articles.

4. A device as called for in claim 2, wherein the means for elevating the trailing edge of the article last deposited on the conveyor comprises a rotatable shaft having a lifter finger projecting therefrom to engage the undersurface of the said article last deposited on the conveyor at a location adjacent but in advance of the trailing edge of said article, said elevating means elevating the trailing edge and rear portion of said article in timed sequence with the advance of the leading edge of the next advanced article.

5. A device as called for in claim 2, wherein the individual articles are consecutively numbered with each suceeding article having a number one unit higher than the preceeding article, and wherein the articles as delivered in underlap echelon relation on the conveyor are disposed in an ever increasing consecutive numerical order.

6. A device as called for in claim 2, wherein limiting means are provided at the upstream end of the conveyor for limiting the amount by which the leading edge of each succeeding article is advanced under and relative to the under-surface of the preceding article last deposited on the conveyor.

7. A device as called for in claim 6, wherein said limiting means includes a rotatably driven slow down roll the periphery of which exerts pressure against the upper surface of the last article deposited onto the conveyor, intermediate the length of said article to provide an abutment transversely of said article which is engaged by the leading edge of the next succeeding article as it is advanced beneath and forwardly of the trailing edge of the preceding article.

8. A method of providing an underlap echelon relationship to a plurality of similar sized sheet-like articles which comprises the steps of:
providing a continuously moving article receiving, supporting and conveying surface;
sequentially advancing the leading edge of each of a plurality of similar sized sheet-like articles onto the upstream end of the moving article-supporting surface;
rotating a shaft having a lifter finger projecting therefrom about an axis positioned below the article-supporting surface in timed relationship to the rate of movement of said conveying surface and engaging the undersurface of an article last advanced onto the moving article-supporting surface at a location adjacent to but in advance of the trailing edge of said last advanced article;
advancing the leading edge of the next successive sheet-like article onto the upstream end of the moving article supporting surface in timed sequence with the elevation of the article engaged by said lifter finger so that the leading edge of said next successive sheet-like article is positioned under said elevated trailing edge;
limiting the amount by which the leading edge of each succeeding article is advanced under and relative to the undersurface of the preceding article last deposited on the conveyor by exerting pressure against the last article deposited on the conveyor intermediate the length of the last deposited article to provide an abutment transversely of said article which is engaged by the leading edge of the next succeeding article as it is advanced beneath and forwardly of the trailing edge of the succeeding article; and
altering the amount by which the leading edge of each succeeding article is advanced by exerting pressure against the last article deposited on the conveyor at a location which is moved toward and away from the upstream of the conveyor.

9. The method as called for in claim 8, which includes, prior to step b, step e of repetitiously severing a moving endless web of material into the similar sized sheet-like articles referred to in step b.

10. The method as called for in claim 9, which includes, prior to step e, step f of consecutively numbering those portions of the endless web of material which comprise each of the sheet-like articles which are severed from the web of material in step e.

11. The method as called for in claim 10, which includes the step of slowing the rate of travel of each sheet-like article whose leading edge is advanced as in step f to the rate of travel of the moving article supporting surface.

12. The method as called for in claim 9, wherein the rate of travel at which the sheet-like articles of step d, are individually advanced exceeds the rate of travel of the moving endless web of step e.

13. The method as called for in claim 8, which includes the additional step f of advancing each of the sheet-like articles in step d at a rate of travel which exceeds the rate of travel of the moving article-supporting surface of step a.

14. The method as called for in claim 8, which includes the step of limiting the amount by which the leading edge of each successive sheet-like article is advanced under the rear portion of a preceding sheet-like article.

* * * * *